United States Patent
Graindorge

(10) Patent No.: US 6,778,859 B2
(45) Date of Patent: Aug. 17, 2004

(54) PROCESSING AND MEMORIZING IN A DIFFERENTIATED FORM ACQUIRED DATA RELATING TO HOLTER FUNCTIONS, IN PARTICULAR IN AN ACTIVE IMPLANTABLE MEDICAL DEVICE

(75) Inventor: Laurence Graindorge, Chatenay Malabry (FR)

(73) Assignee: Ela Medical, Montrouge (FR)

( * ) Notice: Subject to any disclaimer, the term of this patent is extended or adjusted under 35 U.S.C. 154(b) by 323 days.

(21) Appl. No.: 10/118,624

(22) Filed: Apr. 5, 2002

(65) Prior Publication Data

US 2002/0173829 A1 Nov. 21, 2002

(30) Foreign Application Priority Data

Apr. 6, 2001 (FR) .......................................... 01 04660

(51) Int. Cl.⁷ ................................................. A61B 5/00
(52) U.S. Cl. ....................................................... 607/59
(58) Field of Search ............................... 600/509, 510, 600/523; 607/9, 27, 59

(56) References Cited

U.S. PATENT DOCUMENTS

| | | | |
|---|---|---|---|
| 5,487,755 A | | 1/1996 | Snell et al. |
| 5,522,850 A | | 6/1996 | Yomtov et al. |
| 5,732,708 A | * | 3/1998 | Nau et al. ................. 600/523 |
| 5,908,392 A | | 6/1999 | Wilson et al. |
| 6,007,493 A | | 12/1999 | Ericksen et al. |
| 6,526,314 B1 | * | 2/2003 | Eberle et al. ............. 600/523 |

* cited by examiner

Primary Examiner—George Manuel
(74) Attorney, Agent, or Firm—Orrick, Herrington & Sutcliffe LLP

(57) ABSTRACT

Apparatus and process for processing and memorizing in a differentiated form data relating to data recorded over a long time period, in particular in an active implantable medical device, more particularly, Holter functions. This process includes the steps of:

a) memorizing in a first memory sector (10) a detailed representation of the data, e.g., Holter data (14, 16, 18, 20), over a plurality of short successive time periods (22), in particular one hour intervals, these intervals following one another over a longer but still short or intermediate time period, corresponding in particular to a one day interval;

b) periodically, reading in the first memory sector the detailed representation and processing the data so as to work out over the intermediate time period (24), in particular a one day period, a consolidated representation of the data recorded over the successive shorter intervals constituting the aforementioned short or intermediate period;

c) cumulatively memorizing in a second memory sector (12) the consolidated representation, to give a representation of the data over a series of the intermediate periods (24) following one another over a relatively long time period, in particular a period of several days or several months; and d) freeing a portion of the first memory sector to allow to memorize therein another detailed representation of new data for the plurality of successive short time periods for the following intermediate period.

15 Claims, 1 Drawing Sheet

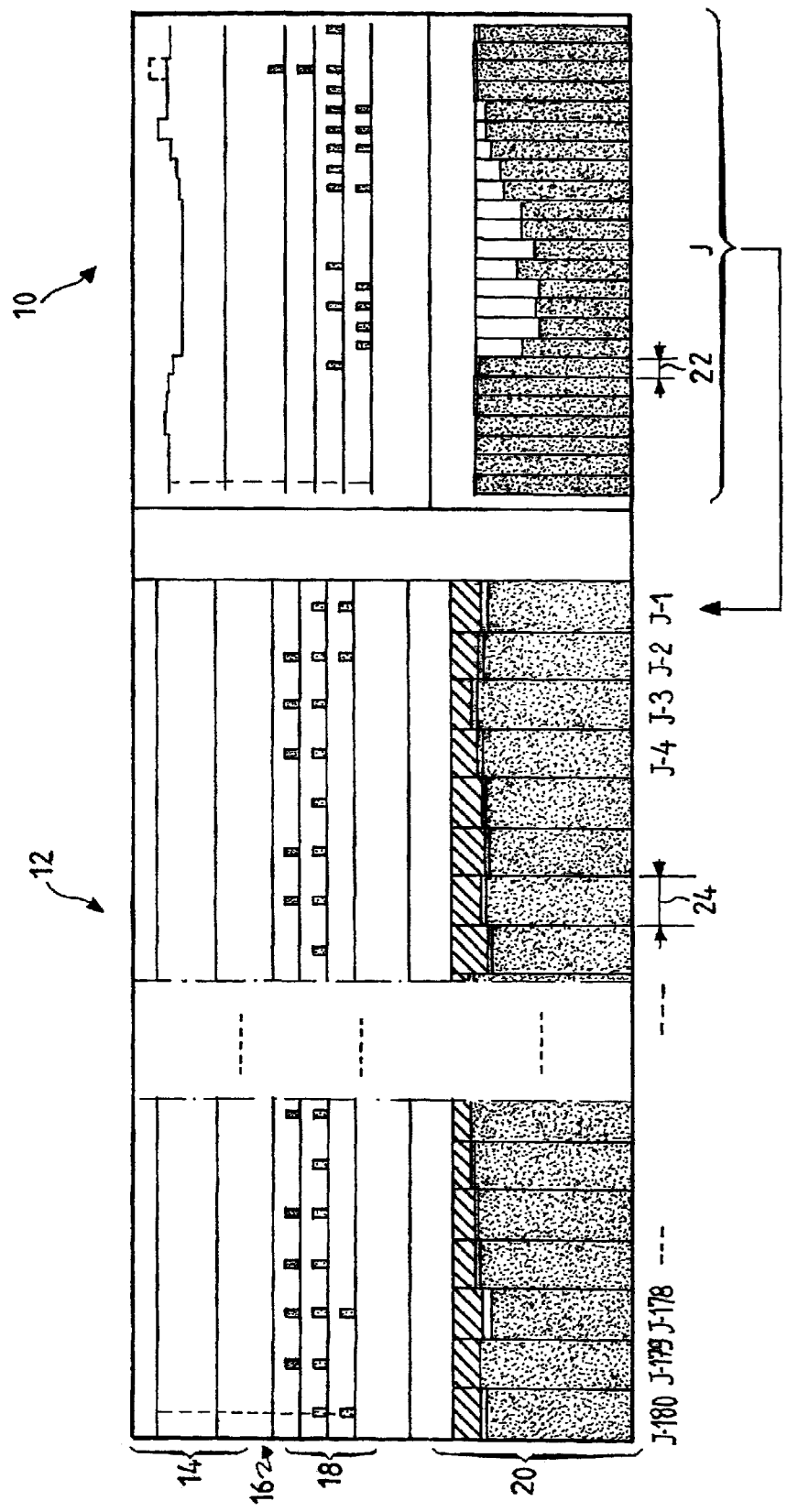

PROCESSING AND MEMORIZING IN A DIFFERENTIATED FORM ACQUIRED DATA RELATING TO HOLTER FUNCTIONS, IN PARTICULAR IN AN ACTIVE IMPLANTABLE MEDICAL DEVICE

FIELD OF THE INVENTION

The present invention is directed to "active implantable medical devices" as such devices are defined by the Jun. 20, 1990 directive 90/385/CEE of the Council of the European Communities. This definition includes pacemaker, defibrillator, cardiovertor and/or multisite devices for the treatment of the disorders of the cardiac rhythm, but also includes neurological apparatuses, medical substance diffusion pumps, cochlear implants, implanted biological sensors, etc., as well as the devices for the measurement of pH or an intra-corporal impedance (such as the measurement of the transpulmonary impedance or the intracardiac impedance).

The invention more particularly relates to the functions of processing and recording data over a long period of time, several days to several months and particularly for so-called "Holter data" relating to the cardiac activity of a patient.

BACKGROUND OF THE INVENTION

The present description refers mainly to the so-called and well known Holter functions that are controlled by implanted devices such as pacemaker, cardiovertor or defibrillator devices, in particular by the implanted device that can be interrogated subsequently by telemetry by use of an external device known as a "programmer."

The invention, however, also can be applied to the case of a simple external Holter apparatus, having for its only function the monitoring and the recording of the cardiac activity.

In the same manner, although the description mainly refers to the cardiac signals collected by means of implanted electrodes, the functions performed by the invention also can be applied to other signals collected (sensed) by implanted as well as external electrodes, as well as to event counters or to signals that are not collected but are representative of a state or an action of the implant or of the patient, for example, the application of a shock therapy, the measurement of an impedance of a lead, etc.

The storage of these various data can be carried out in various ways.

A first technique, known as cumulative storage, involves preserving the data in an undifferentiated manner during the whole of the recording period (typically, over a six-month period for patient follow-up). This storage technique includes time-stamping each event using a marker that will be used as a temporal reference mark when the data are processed after being read by the programmer, so as to reconstitute the chronology of the various successive events recorded. This technique is economical in terms of the required memory size, but it is limited to the memorizing (recording) of specific events and does not allow one to monitor (and record) parameters that are continuously varying, for example, to study the evolution of the average heart rate, of an impedance, or of an index of apnea, etc.

Another technique concerns allotting a memory field to each interval of time (typically one day), where the data corresponding to each one of these periods are memorized, in particular for monitoring the evolution of continuously varying parameters. By allotting a memory field for the data collected during the same day, one can thus store such data over an extended period of time, typically up to six months, day by day. After the reading of the data by the programmer, it is possible to carry out a certain number of data-processing treatments, of a statistical nature or otherwise, relatively complete treatments insofar as the data were preserved identically over the whole duration of the six months period. On the other hand, this technique requires large memory resources because of the very great number of memory fields that would be necessary, for example, approximately 6×30= 180 memory fields for a history over six months (assuming 30 days per month) such that each field would store the data collected over 24 hours.

A compromise must therefore be made between the total period of coverage and the precision of the memorized data within each time period: if one wants a precise follow-up, one can, for example, record 2 day periods, but the whole of the recording will cover only one month (14×2 days); if on the other hand one wants to cover a longer time period, for example, six months, it will be necessary to choose less precise time periods, for example, one week.

OBJECTS OF SUMMARY OF THE INVENTION

The invention proposes an apparatus and a process of processing and memorizing data to be recorded over a long period of time, including but not limited to Holter data, making it possible to overcome these various disadvantages, in particular by optimizing the occupation of the memory. Memory size is a particularly constraining parameter in a miniaturized and implanted medical device.

Broadly, the present invention proposes to carry out a differentiated storage of the short-term data and the long-term data. In one embodiment, the short-term data are memorized over a first time period that is relatively short with a relatively high degree of resolution (for example, data are stored in a series of short blocks of time, e.g., one hour, covering one or two days by the time period of one hour), while the long-term data are stored over a second time period that is a relatively long period with a lower degree of resolution (for example, data covering a six month period is stored by one day time periods).

One of the starting points of the present invention is the inventor's observation that, when Holter data recorded in an implant are analyzed, the precision of the data is important only over the few hours which immediately precede the interrogation, i.e., the reading of the memorized data by the remote programmer, whereas over the weeks or the months which precede those few hours only the general trend of the Holter data and the evolution of such parameter(s) is important to evaluate. For example, if a diagnosis is carried out following a defibrillation shock applied by the apparatus, it will be essential to have a detailed summary of the events which have occurred during a defined period immediately preceding the shock, e.g., 24 or 48 hours or more, in particular including the chronology of the events. For the period prior to the defined period, an analysis of the trend of the events will be generally sufficient.

Indeed, it is believed to be more important to have a follow-up for the time preceding the consultation because: (i) if the patient consults a physician or therapist for a symptom or an awkward or undesirable event, it is extremely probable that this event is recent, and (ii) at the time of the interrogation of the patient, the present invention permits memorizing and reading data reflecting more precise indications over the defined time period (typically one or two days which preceded the consultation and interrogation as compared to data that was recorded 3 or 4 months ago. In other words, the precision of the recording follows the precision of the memory of the patient.

This differentiated storage data recorded over time implies a periodic update of the memory. In one example, during the defined time period, the data is recorded on an hour by hour basis. At the end of the defined time period, each of the hourly recordings are consolidated into data representative of the defined time period. Then, a number of such consolidated data corresponding to successive defined time periods are stored in memory to cover a long term time period. Similarly, new data are recorded hourly as the next defined time period elapses. As the long term period is reached, the oldest consolidated data is replaced by the consolidated data from most recent defined time period. In another embodiment, the data representations are stored by short time periods of one hour over a defined period of one day, and then every day these data of the short time periods are consolidated, i.e., condensed into a consolidated data representing the defined one day period of time. Then, a number of the consolidated data are retained over a longer time period of a corresponding number of days (which may be days, weeks or months). In this manner, one obtains two recordings having sliding and overlapping time windows (one in the short-term and the other in the long-term), which makes it possible to have a condensed long-term follow-up providing the general trends, and a short-term follow-up that is more precise on the most recently occurring events. The size of the memory to be used will be important in selecting the length of the short term, defined, and long term periods.

One preferred embodiment of the invention proposes a process for storing data in a differentiated manner characterized by the steps of:

a) memorizing in a first memory sector a detailed representation of the data over a first plurality of first time periods the first plurality of first time periods following one another over a second time period, preferably the first time periods are successive one hour intervals and each second time period is the defined time period and is one day;

b) periodically, reading in the first memory sector the detailed data representation and processing said detailed data representation to produce, over a third time period, a consolidated representation of the data memorized over said first plurality of first periods, preferably the third time period is a daily interval corresponding to the second period;

c) cumulatively memorizing in a second memory sector the consolidated representations, to give a representation of the data over a plurality of third time periods following one another over a fourth period, preferably, the fourth time period is a period of several days or several months, and the third time periods are successive; and d) freeing a portion of the first memory sector to allow to memorize therein a detailed representation of new data for another second period.

It should be understood that the second and third time periods may be the same interval, e.g., one day.

In a preferred embodiment, steps b) with d) can be carried out at the end of each second time period, such that the consolidated representation stored at step b) is elaborated starting from the data of the penultimate second time period, so that the detailed representation over the most recent second time period remains stored.

The detailed representation of the data can in particular include:

elaborating a histogram of values over the successive first intervals, i.e., short intervals, with the processing at step b) including the addition of the values to form a consolidated histogram;

values of a parameter measured during each successive first time period, ie., the short time period, with the processing at step b) including the calculation of an average value of the measured values, or alternately the selection of the minimum value and/or maximum value reached by the measured values during the second time period;

an indicator of the occurrence of an event, or presence of a state of operation of the device or of the patient, during each successive first time period, i.e., the short interval, with the processing at step b) including the positioning of a marker in the event of the presence of at least one of the aforesaid indicators during the second time period, or the determination of a number of occurrences of the aforesaid indicator during said second time period.

BRIEF DESCRIPTION OF THE DRAWING

Other features, characteristics, and advantages of the present invention will appear to a person of ordinary skill in the art in view of the following detailed description of preferred embodiments of the present invention, made with reference to the annexed drawing FIG. 1, which shows in the form of a chronogram various data representations and consolidated data stored in memory sectors.

DETAILED DESCRIPTION OF THE INVENTION

With reference to the drawing FIG. 1, in a preferred embodiment the Holter data are stored as representations in the form of two distinct records, namely a first record 10 containing the data representations of the most recent day, with a one hour time resolution, and a second record 12 containing the Holter data consolidations of, for example, the last past 180 days (approximately six months), with a one day resolution. These two records, each having a different level of detail or resolution, make it possible to have a general long-term follow-up (record 12, over six months) supplemented by a higher resolution follow-up in the short term on the most recent events (record 10, over 24 hours). In practice, information is stored by one hour periods of time over one day. The terms "storing," "recording," and "memorizing" are used synonymously and interchangeably herein to mean placing data in a memory sector of a memory device. The term "record" means the information contained in a memory sector.

Periodically, i.e., when one has completed a daily recording in the same way as first record 10, the new Holter data detected are represented and the representations come to replace the preceding daily record 10 which is itself consolidated into a column on the second record 12 having a one day period resolution, and becomes a part of the second record (whose last recording becomes chronologically before the last, etc). Thus, oldest consolidated data is discarded and in this manner the second record 12 maintains a sliding window of the last number of periods J of second or third periods (e.g., days) of consolidated data defining the fourth period (months/weeks) that are the most recent J periods. FIG. 1 illustrates J periods where J=180 days. Typically, the second and third periods are the same. However, a situation exists where one might keep, for example, three days of high resolution data, but consolidate the last two days of data for long-term storage. Other long and short term periods where the second and third periods might be different can be envisioned.

The represented and/or consolidated data can be of several types:

It can be a curve, such as curve 14, displaying the average level of the basic heart rate, the frequency of occurrence of extrasystoles, the atrial impedance, the ventricular impedance, etc.

It can be a marker or other indicator, such as are illustrated on graph 16 or 18, indicating the occurrence or the absence of a given event during the time period considered, for example, an occurrence of an extrasystole, the switching of the implant in a particular operating mode, the application of a particular shock therapy, etc. In the alternative, instead of a simple indicator of the occurrence/absence of an event, it is possible to memorize the number of occurrences of that particular event during the period considered.

It can be a histogram, such as histogram 20, giving, for example, an activity/sleep ratio, the index of apnea, etc.

According to the type of stored information and its importance, one can choose several modes to go back and forth from a first period of time 22 (e.g., a short one hour time resolution) to a second period of time 24 (e.g., a longer one day resolution).

When it relates to curves, according to the particular situation, one can store an average of the 24 hourly values to obtain only one value for a one day period; in alternative or complement, it is also possible to keep the maximum value and/or the minimal value reached by the parameter in question over the 24 hour period.

When it relates to markers, one can store the number of occurrences over the 24 hour period, or a marker indicating the existence of at least one occurrence over the 24 hour period.

When it relates to histograms of values, the 24 one-hour histograms can be added to obtain a histogram over the one day period.

It should be understood that the present invention is preferably implemented in software of a microprocessor controlled implantable medical device and its cooperating programmer device. Suitable implantable devices include, but are not limited to commercial pacemaker products sold under the Talent™ brand, available from Ela Médical, Montrouge, France. Advantageously, the present invention can be downloaded to an already implanted device by its external programmer, in a conventional manner, as software instructions to modify the operation of the already implanted device, for such devices that are able to receive software instructions and to modify its operation in response thereto.

Software and hardware suitable for the acquisition of the Holter data (or other data recorded over a long time) and for creating and the storing, reading, and processing of the representations of the Holter data as described in accordance with the foregoing embodiments are believed to be within the circuit design and programming abilities of persons of ordinary level of skill in the art having familiarity with implantable Holter devices and remote programmer devices, and with non-implantable Holter devices which may or may not work in cooperation with a remote programmer device. Once such external Holter device which may be modified in according with the present invention is the Synetec brand device, available from Ela Medical, Montrouge, France.

One skilled in the art will appreciate that the present invention can be practiced by other than the described embodiments, which are presented for purposes of illustration and not of limitation. Indeed, the time periods and other values discussed are merely preferred parameters as a design choice and not limiting.

I claim:

1. A process for processing and memorizing of data to be recorded over a first period of time, in an active implantable medical device such as a pacemaker, a defibrillator, a cardiovertor and/or a multisite device, characterized by the steps of:

a) memorizing in a first memory sector a detailed representation of said data over a first plurality of second time periods, said first plurality of second time periods corresponding to a third time period shorter than said first time period;

b) periodically, reading in the first memory sector the detailed representation of the data and processing said read data to produce a consolidated representation of the data of said first plurality of second time periods for a fourth time period;

c) cumulatively memorizing in a second memory sector (12) the consolidated representations for a second plurality of fourth time periods, said second plurality of fourth time periods corresponding to the first time period; and d) freeing a portion of the first memory sector to allow the memorizing therein a detailed representation of new data for another first plurality of second time intervals.

2. The process of claim 1 wherein providing the first plurality of second time periods comprises providing a first plurality of one hour periods.

3. The process of claim 1 further comprising providing the third time period as a twenty-four hour day.

4. The process of claim 1 further comprising providing said first time period as a multiple of a number of days.

5. The process of claim 4 further comprising providing the multiple of a number of days as a six month period.

6. The process of claim 1 further comprising providing the fourth period as a multiple of the third period.

7. The process of claim 6 further comprising providing the fourth period to be the same as the third period.

8. The process of claim 7, further comprising performing steps b) to d) at the end of each third period, step b) producing a consolidated representation that is elaborated from the data representation of the penultimate third period, so that the representation detailed over the last third period remains stored.

9. The process of claim 7, wherein the detailed representation of the data further comprises a histogram of values established during each successive second time period for said third time period, and the step b) processing comprises the addition of the values of said histograms.

10. The process of claim 7, wherein the detailed representation of the data comprises values of a parameter measured during each successive second time period for said third period, and the step b) processing comprises calculating an average value of said successive measured values.

11. The process of claim 7, wherein the detailed representation of the data comprises values of a parameter measured during each successive second time period for said third period, and the step b) processing comprises the selection of one of the minimum value and the maximum value from among the successive measured values.

12. The process of claim 7, wherein the detailed representation of the data comprises an indicator of the occurrence of an event during each successive second time period for said third period, and the step b) processing comprises positioning a marker in the event of a presence of at least one of the aforesaid indicators during the third time period.

13. The process of claim 7, wherein the detailed representation of the data includes an indicator of the occurrence of an event during each successive second time period for said third period, and the step b) processing comprises determining a number of occurrences of said indicator during the third time period.

14. The process of claim 7, wherein the detailed representation of the data comprises an indicator of a presence of a state during each successive second time period for said third period, and the step b) processing comprises positioning a marker in the event of a presence of at least one said indicator during the third time period.

15. The process of claim 7, wherein the detailed representation of the data comprises an indicator of a presence of a state during each successive second time period for said third period, and the step b) processing comprises determining the number of occurrences of the said indicator during the third time period.

* * * * *